United States Patent
Nordin et al.

(10) Patent No.: US 8,398,403 B2
(45) Date of Patent: Mar. 19, 2013

(54) TOOTH ROOT CANAL ANCHORAGE ASSEMBLY

(76) Inventors: Harald Nordin, Chernex (CH); Peter Nordin, Chernex (CH)

(*) Notice: Subject to any disclaimer, the term of this patent is extended or adjusted under 35 U.S.C. 154(b) by 1490 days.

(21) Appl. No.: 11/942,745

(22) Filed: Nov. 20, 2007

(65) Prior Publication Data

US 2008/0124682 A1 May 29, 2008

(30) Foreign Application Priority Data

Nov. 27, 2006 (EP) .................................... 06405494

(51) Int. Cl.
*A61C 13/30* (2006.01)
*A61C 5/02* (2006.01)

(52) U.S. Cl. ........................................................ 433/220

(58) Field of Classification Search .................. 433/220, 433/173, 174, 175, 180, 183, 201.1, 218, 433/221, 102, 165
See application file for complete search history.

(56) References Cited

U.S. PATENT DOCUMENTS

| | | | | |
|---|---|---|---|---|
| 238,334 | A * | 3/1881 | Bonwill | 433/220 |
| 352,785 | A * | 11/1886 | Sheffield | 433/220 |
| 616,302 | A * | 12/1898 | Evans | 433/221 |
| 4,400,160 | A * | 8/1983 | Lustig et al. | 433/224 |
| 4,505,679 | A * | 3/1985 | Gutentag | 433/224 |
| 5,052,930 | A * | 10/1991 | Lodde et al. | 433/173 |
| 5,518,399 | A * | 5/1996 | Sicurelli et al. | 433/220 |
| 5,595,486 | A * | 1/1997 | Manocha | 433/224 |
| 5,658,145 | A * | 8/1997 | Maillefer et al. | 433/102 |
| 5,779,476 | A * | 7/1998 | Roetzer et al. | 433/166 |
| 5,989,032 | A * | 11/1999 | Reynaud et al. | 433/224 |
| 6,135,775 | A * | 10/2000 | Weisman | 433/220 |
| 6,206,695 | B1 * | 3/2001 | Wong et al. | 433/102 |
| 6,450,815 | B1 * | 9/2002 | Weisman | 433/220 |
| 7,270,541 | B1 * | 9/2007 | Johnson | 433/102 |
| 7,341,453 | B2 * | 3/2008 | Coatoam | 433/173 |
| 7,731,498 | B2 * | 6/2010 | McSpadden | 433/102 |
| 7,785,174 | B2 * | 8/2010 | Badoz et al. | 451/48 |
| 2003/0031981 | A1 * | 2/2003 | Holt | 433/173 |
| 2003/0232309 | A1 * | 12/2003 | Dinkelacker | 433/173 |
| 2003/0235805 | A1 * | 12/2003 | Lax | 433/220 |
| 2008/0227053 | A1 * | 9/2008 | Payen De La Caranderie | 433/102 |

FOREIGN PATENT DOCUMENTS

| | | |
|---|---|---|
| CH | 652 910 | 12/1978 |
| EP | 0 037 864 | 4/1980 |
| EP | 0 083 028 | 12/1982 |
| EP | 0 245 878 | 1/1983 |

(Continued)

OTHER PUBLICATIONS

European Search Report dated Jun. 27, 2007.

*Primary Examiner* — Ralph Lewis
(74) *Attorney, Agent, or Firm* — Ostrolenk Faber LLP

(57) ABSTRACT

The tooth root channel anchorage assembly comprises a core member to be fixed within the tooth root channel and a post to be inserted into the core member having a thoroughgoing bore. The core member comprises a crown part and an anchorage part to be fixed within the root canal, the surface of the anchorage part having a substantially hyperbolic form. Preferably the crown part of the core member as well as a part of the surface of the post have also a substantially hyperbolic form. The hyperbolic form allows a better anchoring and distributing of the load, thus reducing the danger of breaking of the post and root canal, still allowing the access to the root canal before the post is inserted.

8 Claims, 2 Drawing Sheets

FOREIGN PATENT DOCUMENTS

| | | |
|---|---|---|
| EP | 0 113 792 | 7/1984 |
| EP | 0 245 878 | 11/1987 |
| EP | 0 780 100 | 6/1997 |
| FR | 2 716 795 | 3/1994 |
| WO | WO 92/16157 | 10/1992 |
| WO | WO 96/25119 | 8/1996 |
| WO | WO 96/29017 | 9/1996 |
| WO | WO 2006/008121 | 1/2006 |

* cited by examiner

FIG. 1
FIG. 2
FIG. 3
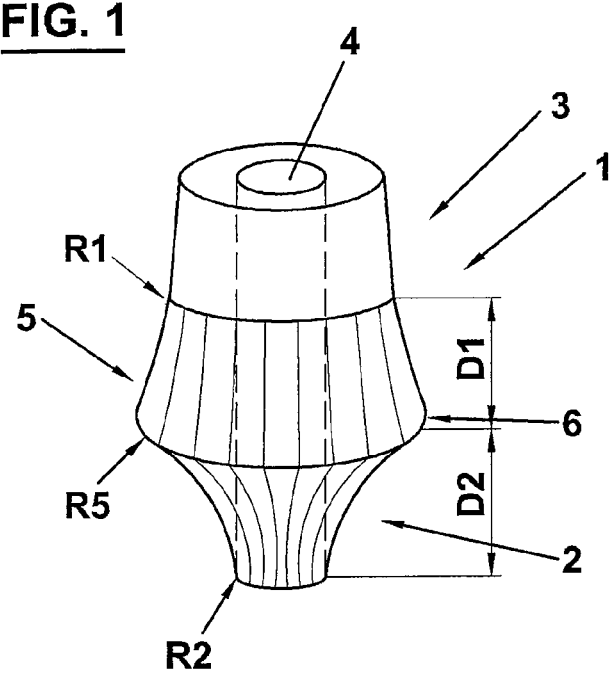
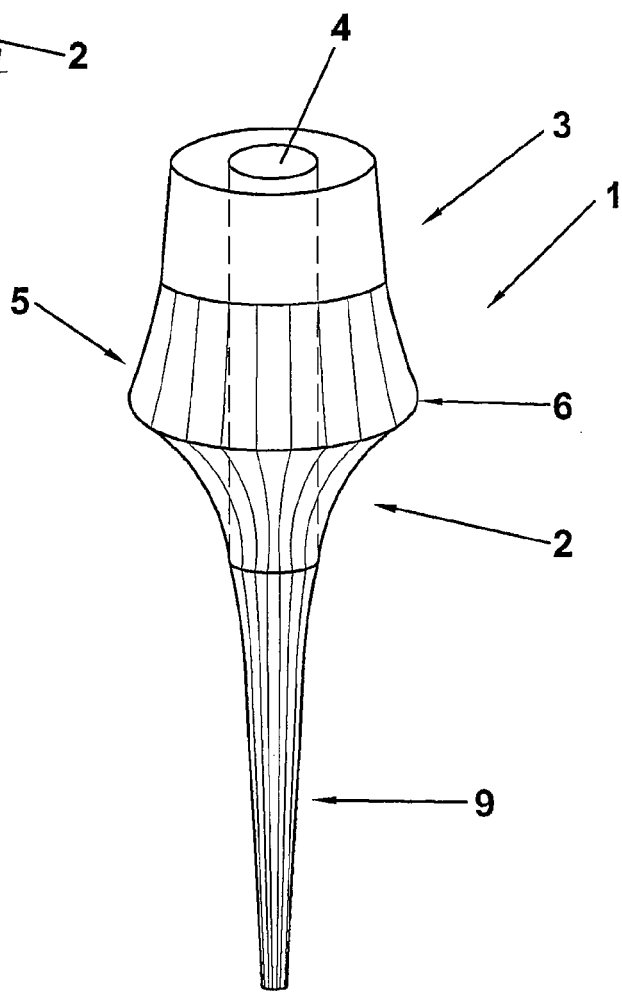
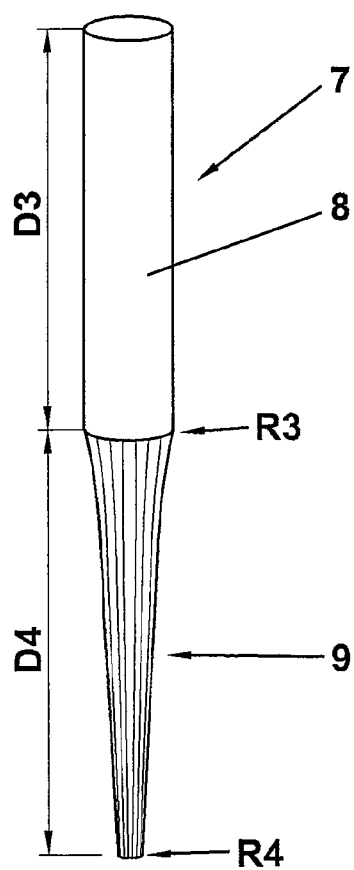

TOOTH ROOT CANAL ANCHORAGE ASSEMBLY

TECHNICAL FIELD

The present application pertains to a tooth root canal anchorage assembly, comprising a core member to be fixed within the tooth root channel and a post to be inserted into the core member, the core member having a thoroughgoing bore.

BACKGROUND OF THE INVENTION

Tooth root canal posts, screws or anchors have existed in dentistry since ca 1750. These items are inserted in the tooth root canal and serve as retention or anchorage for a re-building of the ruined tooth crown, which had to be done, using a plastic material.

To avoid the need for the dentist to build up the core in plastic material, posts with fixed crown cores, in addition to the ordinary posts, were introduced in the early 1900, so Davis posts, ca 1920 and Kurer crown posts ca 1970. They all consist of a large cylinder or head part to serve as crown core and a post or anchor part attached to the bottom of the crown part, the anchor part to be inserted in the root canal.

All these posts show a disadvantage in that there is a point of breakage in the junction between the head and the much narrower root part. There is also no possibility to regulate the length of the root post except cutting it off at the end, thereby with the danger of cutting off special features provided at the point of this part. It is also known that threaded dowels have tendency to fracture and also tight fitting dowels have tendency to exert lateral forces when it is cemented.

Another aspect of root canal treatments is that there is a need to give access to the root canal for preparation and reconstruction before closing definitively the root canal with a post. To this end, inserts or sleeves are fixed in the tooth, having a bore with a greater diameter than the root canal. After the last treatment, a post is inserted into the bore of the sleeve. This sleeve can also serve to fix a rubber dam.

EP-A2-0 245 878 and EP-A1-0 113 792 disclose a tooth root canal anchorage assembly according to the introduction of claim 1 of the present invention, wherein a sleeve as core member with a through bore is cemented into a corresponding hole extending around the root canal. A post, having also a through bore is inserted in the sleeve and fixed into the root canal. The sleeves disclosed are cylindrical, with a collar and the posts are conventional ones with a conical anchoring part. The disclosed shape of the sleeves call for drilling a cylindrical bore with a relatively large diameter, leading to weaken the tooth.

SUMMARY OF THE INVENTION

Starting from this known prior art it is an object of the present invention to provide for a tooth root canal anchorage assembly which core member is shaped to allow a better anchorage whilst weakening less the tooth. This object is attained by the anchorage assembly, wherein the core member comprises a crown part and an anchorage part to be fixed within the root canal, the surface of the anchorage part having a substantially hyperbolic form.

It is a further object of the present invention to provide for a post which shape diminishes considerably the danger of its breaking. This object is attained with the anchorage assembly, wherein the post has a cylindrical part fitting slidably into the bore of the core member, which cylindrical part is followed by a post anchorage part, which surface has a hyperbolic form. Further advantages and objects are defined in other dependent claims.

BRIEF DESCRIPTION OF THE DRAWINGS

The invention will be explained in more detail hereinafter with reference to drawings of an exemplary embodiment.

FIG. 1 shows schematically an embodiment of a core member according to the invention, FIG. 2 shows a post according to the invention, FIG. 3 shows the post of FIG. 2 inserted in core member of FIG. 1.

DETAILED DESCRIPTION OF THE INVENTION

Figure 4:
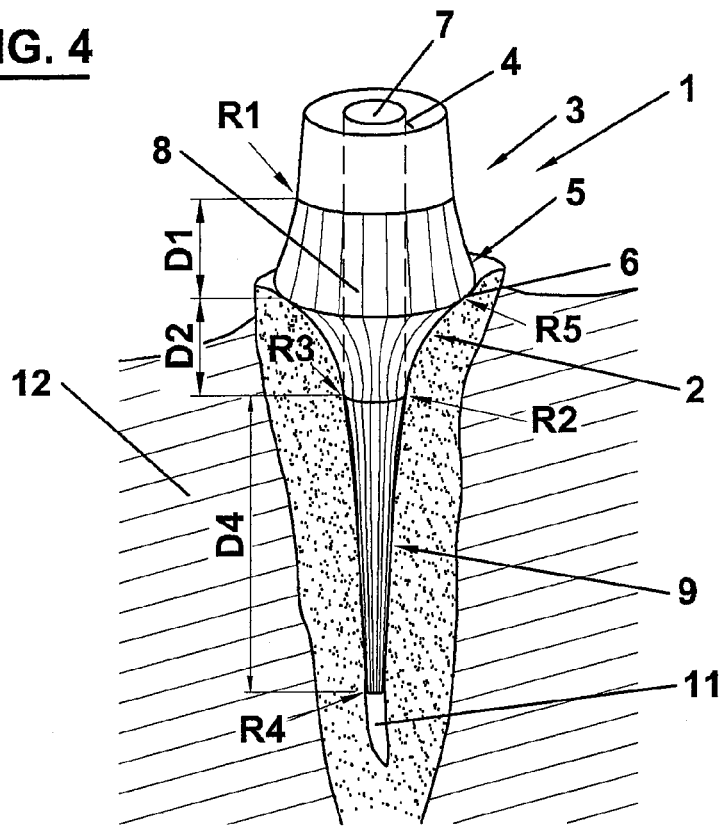
FIG. 4 shows the assembly of FIG. 3 fixed within the root canal of a tooth.
Figure 5:
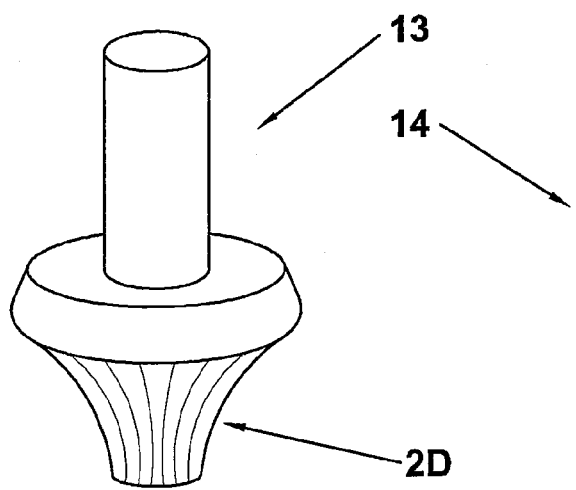
FIG. 5 shows schematically a drill according to the invention.
Figure 6:
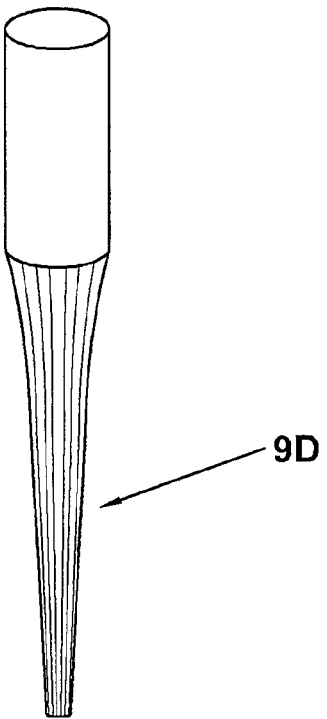
FIG. 6 shows schematically a reamer according to the invention.

The core member 1 of FIG. 1 comprises—see also FIG. 4—an anchorage surface 2, a crown surface 3 and a through bore 4. The crown surface 3 comprises a conical part for receiving a crown or the like, followed by a transfer part 5 with a hyperbolic form ending in a ring face 6 having the greatest diameter of the core member. The anchorage surface 2 has also a hyperbolic form.

Both hyperboloids are hyperboloids of revolution of one sheet. These hyperboloids of revolution are defined as $$\frac{x^2}{a^2} + \frac{y^2}{b^2} - \frac{z^2}{c^2} = 1 \tag{1}$$

whereby a=b. The opening of the hyperbola, resp. the angle α of the asymptote is defined as $$\alpha = \frac{c}{b}.$$

For the present case of a core member, where a=b these values can be calculated on the basis of the parameters given below.

In architecture, hyperboloids are known since the 19th century and in modern time some chimneys of nuclear power plants have also the shape of a hyperboloid.

As follows from FIG. 4, the hyperbolic shaped anchorage surface 2 has the advantage to require a minimal removal of the wall of the root canal, causing its minimal weakening.

The hyperbolic shape of surface 3 allows a better transmittal of the forces bearing on the crown to the core member.

It is understood that the values of a=b, and c for crown surface 2 are not necessarily the same as for anchorage surface 3.

As examples the following values for the greatest diameter R5 of ring face 6 and the smallest diameter R1 of the crown surface 2 and R2 of anchorage surface 3 are as follows:

R1=2-4 mm
R2=1.5-3 mm
R5=3-5 mm

The distance D1 between the beginning of the transfer part 5 and the ring face 6 can be 1.5-3 mm, and D2 between the ring face 6 and the end of the core member can be 1.5-3. mm.

The post 7 comprises a cylindrical part 8 to be received in bore 4 of the core member, followed by an anchorage part 9, which surface can also have a hyperbolic shape with the following values, where a=b:
R3=1-2 mm
R4=0.3-0.7 mm
The distance D3 between R3 and R4 is 8-12 mm.

The hyperbolic surfaces of the crown and anchoring part and of the post allow the optimal distribution of pressure or stress and prevents post, core member or root fractures.

In FIG. 4 the assembled core member and post is shown cemented into the root canal 11 of tooth 12.

The whole assembly comprises a calibrated drill or reamer 13 with reaming or drilling part 2D having the same shape as the core member part 2 for giving the root canal the hyperbolic shape which corresponds to the shape of the anchorage part of the core member and a calibrated drill or reamer 14 which drilling or reaming part 9D corresponds to the anchorage part 9 of the post.

The assembly of the invention allows for multiple ways of application:

1) The post can be fixed and cemented into the core member prior to insertion in the root canal, thereby it is possible to adjust it's length, resp. to have the same length as the core member in the crown part.

2) The post can be inserted first within the root canal and the core member is then sledded down the post till it reaches it's prepared seat in the upper part of the root canal.

3) The core member can be cemented first in the root canal and the post can be sledded through bore 4 into the root canal and the cylindrical part 8 of the post is—after adjusting its length—cemented within bore 4.

4) In some cases, the post can be used alone, without using the core member in teeth having particular roots or multi roots.

Although it is possible to produce the core member and the post of metal, usually stainless steel, as known in the prior art, it is preferable to produce the said parts of glass fibre reinforced composite material, for example as disclosed in U.S. Pat. No. 6,402,519 to the same applicant.

What is claimed is:

1. A tooth root channel anchorage assembly, comprising:
a core member configured to be fixed within the tooth root channel; and
a post configured to be inserted into the core member,
the core member further comprising a thoroughgoing bore, wherein
said core member further comprises a crown part and an anchorage part configured to be fixed within the root canal, and wherein
a surface of the anchorage part has a substantially hyperbolic form, and
the post further comprises:
a cylindrical part configured to slidably fit into the bore of the core member, and
a post anchorage part following the cylindrical part and including a surface with a hyperbolic form.

2. An assembly according to claim 1, wherein the crown part of the core member comprises a surface which has a substantially hyperbolic form.

3. An assembly according to claim 1, wherein the core member and the post are made of fibre glass reinforced composite material.

4. An assembly according to claim 1, wherein said hyperbolic form is a hyperboloid of revolution of one sheet, according to the formula:

$$\frac{x^2}{a^2} + \frac{y^2}{b^2} - \frac{z^2}{c^2} = 1 \tag{1}$$

whereby a=b, and the asymptote is defined as having an angle $$\alpha = \frac{c}{b}.$$

5. An assembly according to claim 4, wherein the core member has the following values:
a=b, a greatest diameter (R5) of the core member=3-5 mm, a smallest diameter (R1) of the crown surface=2-4 mm, a smallest diameter (R2) of the anchorage surface=1.5-3 mm, a distance (D1) between the beginning of the hyperbolic surface and the greatest diameter (R5)=1.5-3 mm, and a distance (D2) between the greatest diameter (R5) and the end of the anchorage part (R2)=1.5-3 mm.

6. An assembly according to claim 4, wherein the post has the following values:
a=b, a diameter (R3) of the cylindrical part=1.3-1.7 mm, a diameter (R4) of the end of the post=0.3-0.7 mm, a distance (D3) between (R3) and (R4)=8-12 mm.

7. An assembly according to claim 1, further comprising a first drill having a first drilling surface with the same shape as the anchorage part of said core member and a second drill having a second drilling surface with the same shape as the post part which is configured to be inserted into the root channel.

8. An assembly according to claim 1, further comprising a first reamer having a first reaming surface with the same shape as the anchorage part of said core member and a second reamer having a second reaming surface with the same shape as the post part which is configured to be inserted into the root channel.

* * * * *